(12) United States Patent
Zavitsanos et al.

(10) Patent No.: US 6,936,813 B2
(45) Date of Patent: Aug. 30, 2005

(54) DYNAMIC LIBRARY SEARCHING

(75) Inventors: A. Paul Zavitsanos, Westchester, PA (US); Philip Leigh Wylie, Kennett Square, PA (US); Chin-Kai Meng, Hockessin, DE (US)

(73) Assignee: Agilent Technologies, Inc., Palo Alto, CA (US)

( * ) Notice: Subject to any disclaimer, the term of this patent is extended or adjusted under 35 U.S.C. 154(b) by 26 days.

(21) Appl. No.: 10/768,041

(22) Filed: Feb. 2, 2004

(65) Prior Publication Data

US 2005/0167581 A1   Aug. 4, 2005

(51) Int. Cl.[7] .......................... G06F 19/00; H01J 49/50
(52) U.S. Cl. ....................... 250/282; 250/281; 250/287
(58) Field of Search ............................... 250/282, 281, 250/287

(56) References Cited

U.S. PATENT DOCUMENTS

| | | | |
|---|---|---|---|
| 6,639,212 B1 * | 10/2003 | Guevremont et al. | 250/282 |
| 2003/0213902 A1 * | 11/2003 | Takahashi | 250/282 |
| 2004/0096982 A1 * | 5/2004 | Barnea et al. | 436/173 |

* cited by examiner

*Primary Examiner*—John R. Lee
*Assistant Examiner*—James J. Leybourne (57) ABSTRACT

Systems and methods for mass spectrometry dynamic library searching are provided for use with mass spectrometer spectra. A composite spectrum is created from multiple spectra. The multiple spectra are collected at varying collision energies from a mass spectrometer. Dynamic searching algorithms are utilized for assigning a degree of importance to ions depending upon the identity of the ions, and for assigning a degree of importance to the ion ratios. A search is performed against a library of composite spectra that includes data for adduct, dimer, and oligomer ions. The systems and methods determine a match quality value that takes into account any or all ions in the spectrum along with the ions' ratios and degrees of importance.

31 Claims, 7 Drawing Sheets

ALL SPECTRA ARE OF M=499 AT L1 VOLTAGE, BUT AT
DIFFERENT TRACE MOBILE PHASE SALTS

FIG. 1A

ALL SPECTRA ARE OF M=499 AT L1 VOLTAGE, BUT AT
DIFFERENT TRACE MOBILE PHASE SALTS

FIG. 1B

ALL SPECTRA ARE OF M=499 AT L1 VOLTAGE, BUT AT DIFFERENT TRACE MOBILE PHASE SALTS

FIG.1C

ALL SPECTRA ARE OF M=499 AT L1 VOLTAGE, BUT AT DIFFERENT TRACE MOBILE PHASE SALTS

LOGIC FLOW CHART
FIG. 3

DYNAMIC LIBRARY SEARCHING

BACKGROUND

1. Field of the Invention

The present invention relates to the identification of compounds in mass spectrometry; and more specifically, the invention addresses the assignment of weighting factors to ion adducts that populate collected spectra.

2. Description of Related Art

A mass spectrometer (MS) is one of the most powerful tools available for quantitative and qualitative analysis of an unknown or suspect compound. One type of mass spectrometer, available since the 1950's, employs electron impact (EI) ionization and fragmentation—whereby vaporized molecules are simultaneously ionized and fragmented with high energy under high vacuum to produce a broad spectrum of ions. EI-MS is typically coupled to a gas chromatograph (GC) to insure adequate molecule separation prior to analysis. Spectra obtained by this technique provide unique spectral "fingerprints" of molecules that are reproducible under set conditions, e.g., 70 eV electron energy and approximately unit resolution.

With the increasing power and availability of computers, large collections, or libraries, of EI-MS spectra have been developed along with associated searching software. Such databases, which may contain hundreds of thousands of molecular fingerprints, are often purchased with the instrument. A typical library search compares the spectrum of an unknown compound with the spectra of known compounds in the library and retrieves "hits" of compounds that have similar spectra.

Unfortunately, GC separation, which is the separation technique usually employed with EI-MS, is not possible with a significant percentage of molecules. GC separation requires that molecules be injected as a vapor. Thus, large, thermally labile molecules are not always suitable for GC analysis. In addition, GC analysis, as often as not, requires extensive and time consuming sample preparation and derivatization. This is especially true in the case of compounds with high polarity and low volatility.

In contrast, liquid chromatography (LC) is a more versatile separation technique. For LC separation, the molecules are injected in solution. Most molecules of interest are more easily solubilized than vaporized. However, LC is not compatible with EI, where the molecule must be introduced into high vacuum as a vapor. Therefore, LC is coupled to mass spectrometers that utilize different mechanisms for ionization, e.g., atmospheric pressure ionization (API).

LC-API-MS is well suited to the investigation of semi-volatile, thermo-labile and polar substances, like pesticides, explosives and forensically relevant substances. Unfortunately, existing EI-MS libraries are not suitable for identifying API-MS spectra. New API-MS libraries must be constructed.

One difficulty in constructing libraries for API-MS is the fact that API, unlike EI, generates little or no fragmentation. It is not uncommon to see only the pseudo molecular ion in the mass spectra. This means that API-MS is an excellent means for identifying the molecular weight of an unknown compound, but it cannot distinguish between the thousands of molecules that have any given molecular weight.

To increase ion fragmentation, collision induced dissociation (CID) is typically used in combination with API-MS. However, CID is highly variable. The ions generated by CID, as well as the ion ratios, can vary between different mass spectrometer models, between instruments of the same model, and between day to day operations on the same instrument. These variations occur, among other things, as a function of the ion source and the highly sensitive nature of the CID region.

One means for addressing the variable nature of API-CID-MS spectra is the use of performance based tuning. Performance based tuning attempts to normalize the difference in CID fragmentation between instruments. However, even when API-CID-MS is used in conjunction with performance based tuning, the fragmentation of the molecules still varies considerably under any given set of conditions. Accordingly, it is known to generate multiple spectra under multiple conditions, which may then be evaluated separately or as part of a composite spectrum that presents the sum or average of the various spectra.

An API MS generated spectrum, or composite spectrum, usually contains a peak for the "pseudo molecular ion," from which the molecular weight can be correctly inferred. Usually this is a protonated molecular ion $[(M+H)]^+$. However, heavier positively charged adducts are often seen that can confuse the untrained observer. For example, salts, such as ammonium ion adducts $[(M+NH_4)]^+$, sodium ion adducts $[M+Na]^+$ and potassium ion adducts $(M+K)^+$ may appear in, or even dominate, the spectrum. In addition, positively charged dimers and oligomers of the parent molecule may appear, e.g., $(2M+H)^+$. These adducts may or may not be present in the spectrum depending upon chromatographic conditions, purity of solvents, pH, etc. The trained analyst can use adducts to confirm the identity of the pseudo molecular ion. But, because adducts are not always present and, when present, vary greatly in abundance, their absence has no particular significance. There remains a need in the art to create methods to identify compounds by API-MS spectra in light of the adducts that may or may not be detected.

SUMMARY OF THE INVENTION

In one embodiment, a method is provided for accounting for adducts in spectra to make library searching more reliable. The method begins by collecting multiple spectra at varying collision energies from a mass spectrometer. Next, the pseudo molecular ion is identified. The multiple spectra are then used to create reduced spectra. A composite spectrum is then created from the reduced spectra. A library is then searched for known composite spectra for the composite spectrum created from the reduced spectra. A match quality value is then assigned that is indicative of a measure of the fit between the composite spectrum and the library of known composite spectra.

Other systems, methods, features, and advantages of the present invention will be apparent to one with skill in the art upon examination of the following drawings and detailed description.

BRIEF DESCRIPTION OF THE DRAWINGS

Many aspects of the invention can be better understood with reference to the drawings. It should be recognized that components in the drawings are not necessarily to scale, emphasis instead being placed upon clearly illustrating the principles of the present invention. It should also be recognized that like reference numerals in the drawings designate corresponding parts from several views. In this light, the following drawings are provided.

DETAILED DESCRIPTION OF PREFERRED EMBODIMENTS

The present invention is a system and methodology utilized to improve reference libraries and searching of reference libraries associated with mass spectrometers. In a liquid chromatograph-mass spectrometer (LC-MS), an unknown compound is received in liquid form in a mass spectrometer and analyzed. The unknown compound may be injected into the mass spectrometer using atmospheric pressure ionization (API). Usually, API returns a spectrum showing a single spectral peak for the pseudo molecular ion. The unknown compound may additionally or alternatively be injected using collision induced dissociation (CID), which fragments the single ion. CID may be used to produce one or more product ions, which may or may not include the parent molecular ion. Fragmentation occurs at different energies for different ions.

In order to produce spectra showing more than a single spectral peak, which represents the molecular ion, the unknown compound may be injected multiple times into the mass spectrometer under different conditions each time, i.e., CID voltage, yielding multiple spectra representing the unknown compound. The CID voltage may be changed several times while a peak elutes so multiple spectra are generated in a single run. Thus, any number of spectra may be collected, each at a different CID voltage.

In one embodiment, the unknown compound may be injected using both API and CID. When the CID voltage is varied with each scan and when varying amounts of fragmentations are induced by the different CID voltages, several spectra will represent the unknown compound. The single spectral peak from the API injection is difficult to search in a library of known spectra. The low information content of API spectra can be combined with the CID spectra to give a single, combined, highly informative spectrum. Preferably, the single combined spectrum, or composite spectrum, includes two to four different spectra from API and CID at various voltages. The composite spectra utilized by the Dynamic Library Searching may be an average of collected spectra, a sum of collected spectra, or a composite spectrum generated via spectral axis transform techniques.

API spectra are plagued by the fundamental phenomenon of adduct formation. The magnitude of these adducts can vary to the point of radically affecting the appearance of the spectrum. The useful ions and ion ratios will not vary greatly regardless of the extent of adduct formation and experienced interpreters of API spectra can appropriately discount such formation. The mass and abundance data is not sufficient to determine what ions are adducts and which ions are not. Only intelligence supplied by the experienced mass spectroscopist can properly assign and make use of this adduct data. Accordingly, in one embodiment, the experience of the spectrocopist may be applied in assigning the correct statistical weightings to an executable program.

Figure 1A:
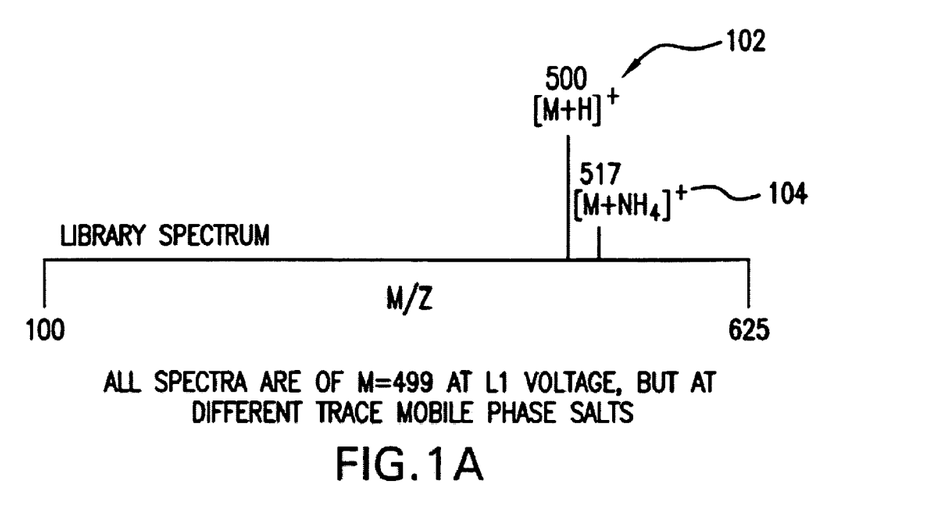
FIGS. 1A–D depict multiple individual spectra that show different spectra collected for the same unknown molecule.
Figure 1B:
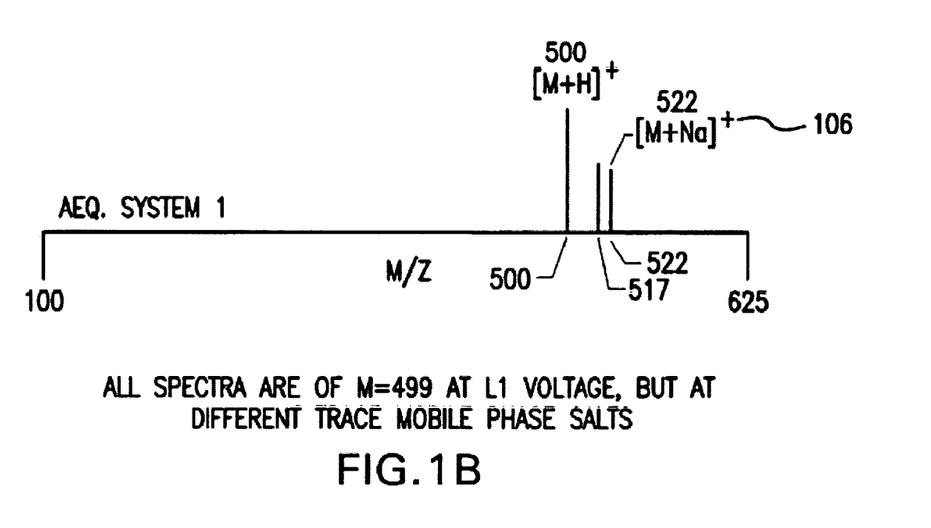
Figure 1C:
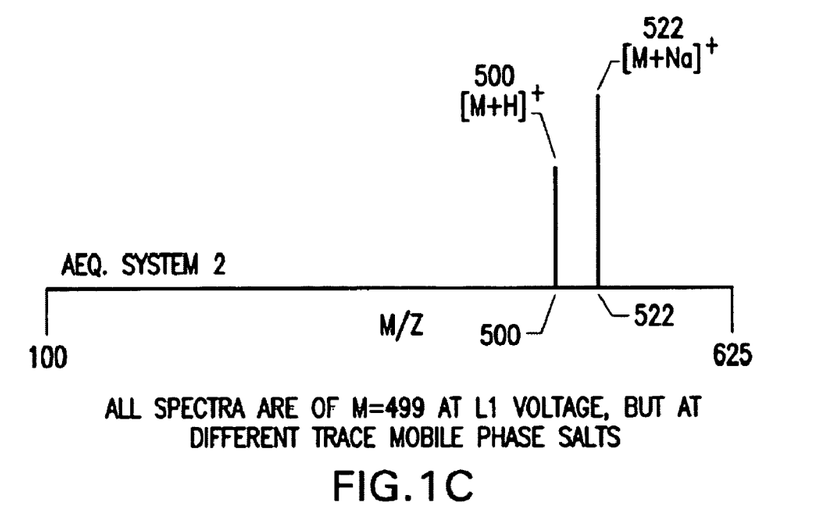
Figure 1D:
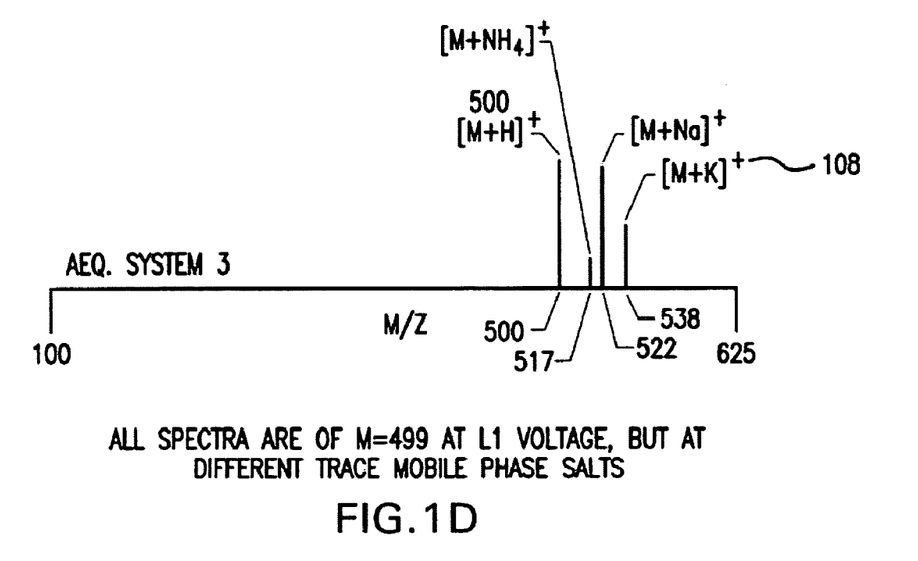

FIGS. 1A–D provide multiple individual spectra, as utilized in one embodiment of the present invention. Each individual spectrum exists on an x-axis. FIG. 1A shows the library spectrum and FIGS. 1B–D show three different spectra that could be generated for the same molecule M. In FIGS. 1A–D M=499 and the spectra are generated at L1 voltage. FIGS. 1B–1D show spectra of M in the presence of different trace mobile phase salts and the different spectra that could result from the different mobile phase salts. The x-axis is the spectral axis and the y-axis shows the relative abundance. For purposes of simplicity the figures set forth in this disclosure do not show the peaks that normally result from the presence of isotopes. The spectra depicted in the figures have been simplified and focus on the most abundant ion of each adduct, dimer, or oligomer. In all examples, the pseudo molecular ion is present, but the presence and abundance of other ions is dependent upon other conditions in the analysis.

FIG. 1A shows the library spectrum for the pseudo molecular ion. The spectrum usually contains a peak for the pseudo molecular ion, from which the molecular weight can be correctly inferred. Usually this is a protonated molecular ion $[(M+H)^+]$ (reference numeral 102) but other charged pseudo molecular ions may be seen. As discussed above, in order to produce multiple spectra representing the unknown compound, the unknown compound may be injected multiple times into the mass spectrometer at different collision energies. FIGS. 1B–D show different spectra that can result from the same molecule M from FIG. 1A. In addition to the pseudo molecular ion, ions of higher mass are often seen that may confuse the untrained user. These consist of positively charged adducts and/or dimers (or oligomers) of the parent molecule. The following ions are typical examples: $(M+NH_4)^+$ (reference numeral 104), $(M+Na)^+$ (reference numeral 106), and $(M+K)^+$ (reference numeral 108). A composite spectrum may be created from the spectra collected at the different collision energies to provide a spectrum with more information related to the abundance and ratios of the fragment ions.

Adducts and dimers may or may not be present in the spectrum depending upon chromatographic conditions, purity of solvents, pH, etc. The trained analyst can use the presence of dimers and adducts to confirm the identity of the pseudo molecular ion. But, since dimers and/or adducts aren't always present, and because their abundance can vary greatly, the absence of adducts and/or dimers has no significance. Thus, the mass and abundance data in present systems is not sufficient to determine what ions are adducts and which ions are not without analyst interpretation. In one embodiment, these shortcomings are overcome by applying the experience of the spectrocopist in assigning the correct statistical weightings to the mass and abundance data. For example, the ratios of adduct, dimmer, and/or oligomer ions to each other or to the pseudo molecular ion may be given a small weighting factor; while the ratios of the pseudo molecular ion and its fragment ions are given a large weighting factor. These assignments may then be used in conjunction with an executable program to assist in the identification of the unknown compound.

Figure 2:
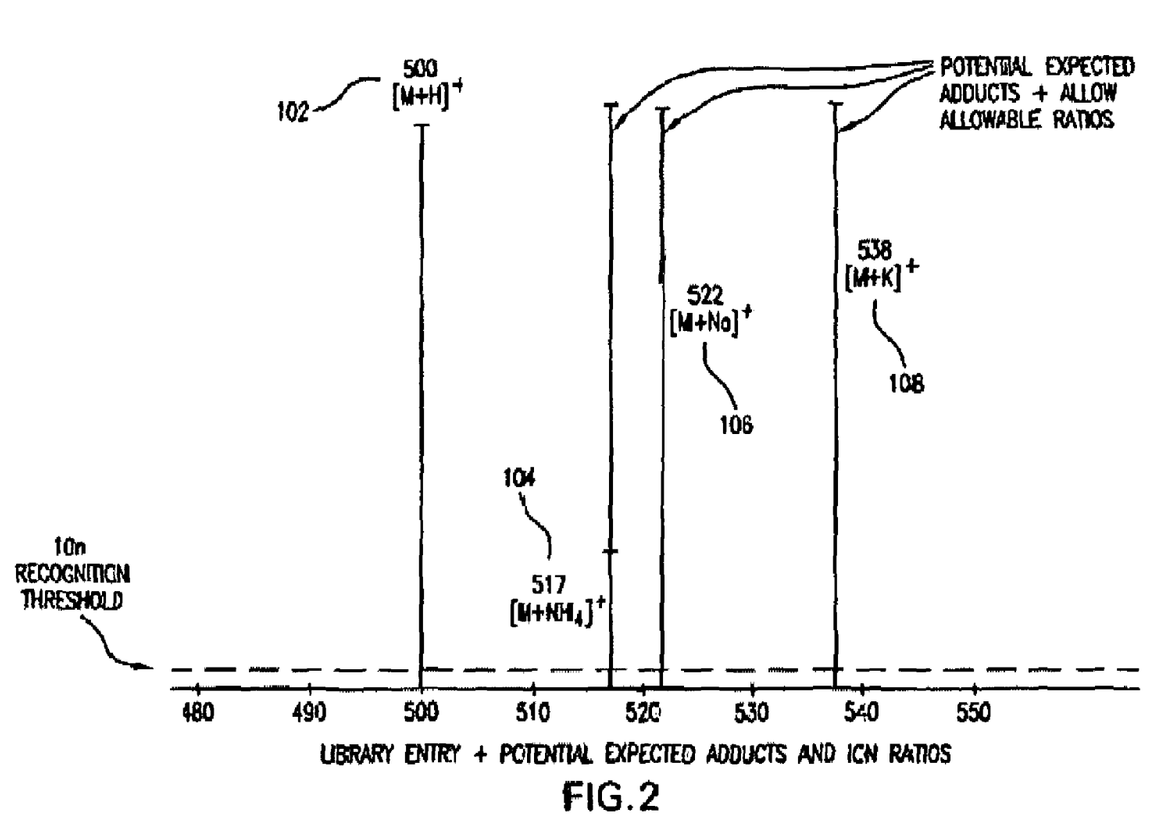
FIG. 2 depicts a spectrum which combines a library entry with potential expected adducts and ion ratios.

FIG. 2 shows a spectrum which combines the library entry (FIG. 1A) with potential expected adducts and ion ratios on the same axis. As in FIGS. 1A–D, the x-axis is the spectral axis and the y-axis is the abundance axis. The pseudo molecular ion 102 is identified by $[M+H]^+$, where m=499. The potential expected adducts 104, 106 and 108 and allowable ratios are also seen on the spectrum, to the right of $[M+H]^+$, and are designated by $[M+NH_4]^+$, $[M+Na]^+$ and $[M+K]^+$.

The presence of adducts and/or dimers (and occasionally larger oligomers) in API spectra can be used to support the pseudo molecular ion assignment 102 and, therefore, the determination of the mass of the parent molecule. As discussed above, spectra may or may not display adducts or dimers (or other oligomers). Thus, the absence of these ions does not preclude assignment of the pseudo molecular ion. The ratios of various adduct and/or dimer (or oligomer) abundances to each other or to the pseudo molecular ion are unimportant. That is, the presence or absence of adducts and/or dimers (or oligomers) and their individual abundances when present, are dependent upon the analytical conditions, which are not necessarily reproducible. Therefore, once the pseudo molecular ion 102 is identified, any ions with higher molecular weight could then be ignored by assigning a weight factor of small significance.

In API spectra, the presence and mass of the pseudo molecular ion 102 are characteristic of the parent molecule. When fragmentation occurs, the mass of these fragments and ion ratios are significant and can be used to help identify the parent molecule. Therefore, these fragments and ion ratios can be assigned a large weighting factor in the analysis. Performance based tuning makes fragmentation reproducible.

The mass assignments allow one to compensate for variations in a compound's API spectrum due to adduct formation. Once an ion mass is recognized as an adduct then weighting factors to reduce the significance of the adduct ions can be applied to the spectral match. At present, no intelligence is applied to weighting specific ions in an API spectrum. Spectral matches are presently performed based entirely on the ion masses and abundance observed. Adduct formation can severely limit the utility of such an approach. The assignment of a degree of importance to the adduct ions increases the power of the search and consequently increases the reliability of the spectral match.

Figure 3:
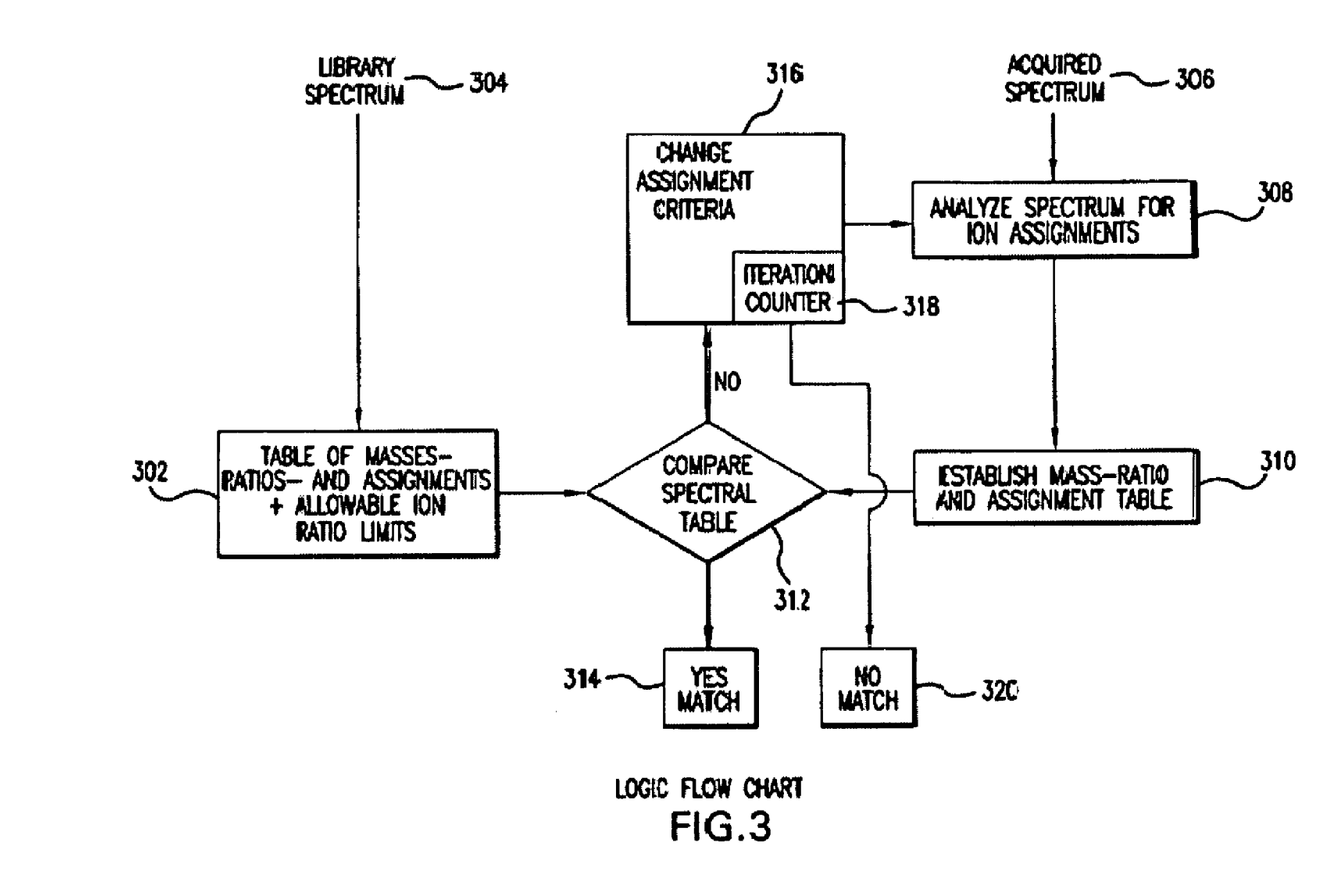
FIG. 3 depicts a logic flow chart of one system for mass spectrometry dynamic library searching.

FIG. 3 is a logic flow chart showing how spectral library searching may identify the parent molecule that has given rise to the spectrum, or categorize the molecule as being similar to a known molecule and/or determine its molecular weight. Specifically, one looks at various ions in a spectrum and assigns to each a likely identity e.g., $(M+H)^+$, $(M+NH_4)^+$, $(M+Na)^+$, $(M+K)^+$, $(2M+H)^+$, etc., as discussed above. This is possible because likely adducts have predictable m/z values. In the case of the ions shown above, the mass assignments would be M+1, M+18, M+23, M+39, and 2M+1, respectively. When present, these ions give added confidence to the assignment of the molecular ion. Fragment ions may or may not occur in the region of the spectrum below the pseudo molecular ion. Once the molecular ion has been tentatively identified, any adduct, dimer, or oligomer ions present can be given a weighting factor, which reflects their contribution to spectral identification. The spectrum can then be searched against a library of known spectra.

The logic flow chart begins with the creation of a table of masses, ratios, assignments and abundance ratios (302) from the library spectrum (304). The table (302) may have a list of allowable limits to make the table more universal. This can help compensate for the fact that ion ratios do not necessarily match exactly from instrument to instrument, day to day, or run to run. The table may also have different weighting factors for the expected adducts that can be applied separately. The table (302) is used to compare the acquired spectrum (306) to determine the identity of the molecular compound. The acquired spectrum may be a composite spectrum that is representative of multiple spectra of the unknown compound collected at different collision energies.

As discussed above, the composite spectrum may be an average of collected spectra, a sum of collected spectra, or a composite spectrum generated via spectral axis transform techniques. The acquired spectrum (306) is analyzed (308), whereby the analysis identifies the pseudo molecular ion, determines the ions that are present and determines a degree of importance or weighting value for the ions present. The steps of identification of the ions and assignment of a degree of importance may be performed by one or more algorithms. Next a table for the acquired spectrum (310) is established. The table (310) establishes the masses, the ratios, and assigns values to the ion(s) and the ion ratios.

Next, the library table (302) is compared to acquired spectrum table (310) to determine whether or not there is a match (312). The process finds the best matches by comparing the unknown to the whole library. If there is a match (314) the process is over. In one embodiment, the process may continue to see if there are other matches. A table of hits may be created and sorted in order of match quality. A match may be determined by reaching a sufficient match quality value between the library table (302) and the acquired spectrum table (310). Similarly, the library table (302) may also be adjusted. For example, the ion ratio allowed ranges may be increased, or the limits reduced in cases where there are too many hits. In addition, the user may want to change the contribution of the adducts, dimmers, etc. Then, the user can use the modified library table (302) in the comparison (312).

If there is no match, the user can change the assignment criteria (316) and start the process over. Thus, the method may be an iterative process. Prior art systems only rely upon abundance and existence of ions; thus, they do not allow for dynamic searching where adjustment may be made to the criteria (316). Deconvolution algorithms may be applied to sort out the spectra from overlapping peaks. The match quality may also be increased by subtracting out some background in the spectrum that results from over lapping peaks. After a certain number of iterations through the process, the iteration counter (318) may determine that there does not exist a match for the unknown compound (320).

The systems and methods, described above, can be implemented in hardware, software, firmware, or a combination thereof. In some embodiments, the systems and methods are implemented in software or firmware that is stored in a memory and that is executed by a suitable instruction execution system (e.g., FIGS. 3, 4 and 5). If implemented in hardware (e.g., FIG. 6), the systems and methods can be implemented with any technology known in the art.

Figure 4:
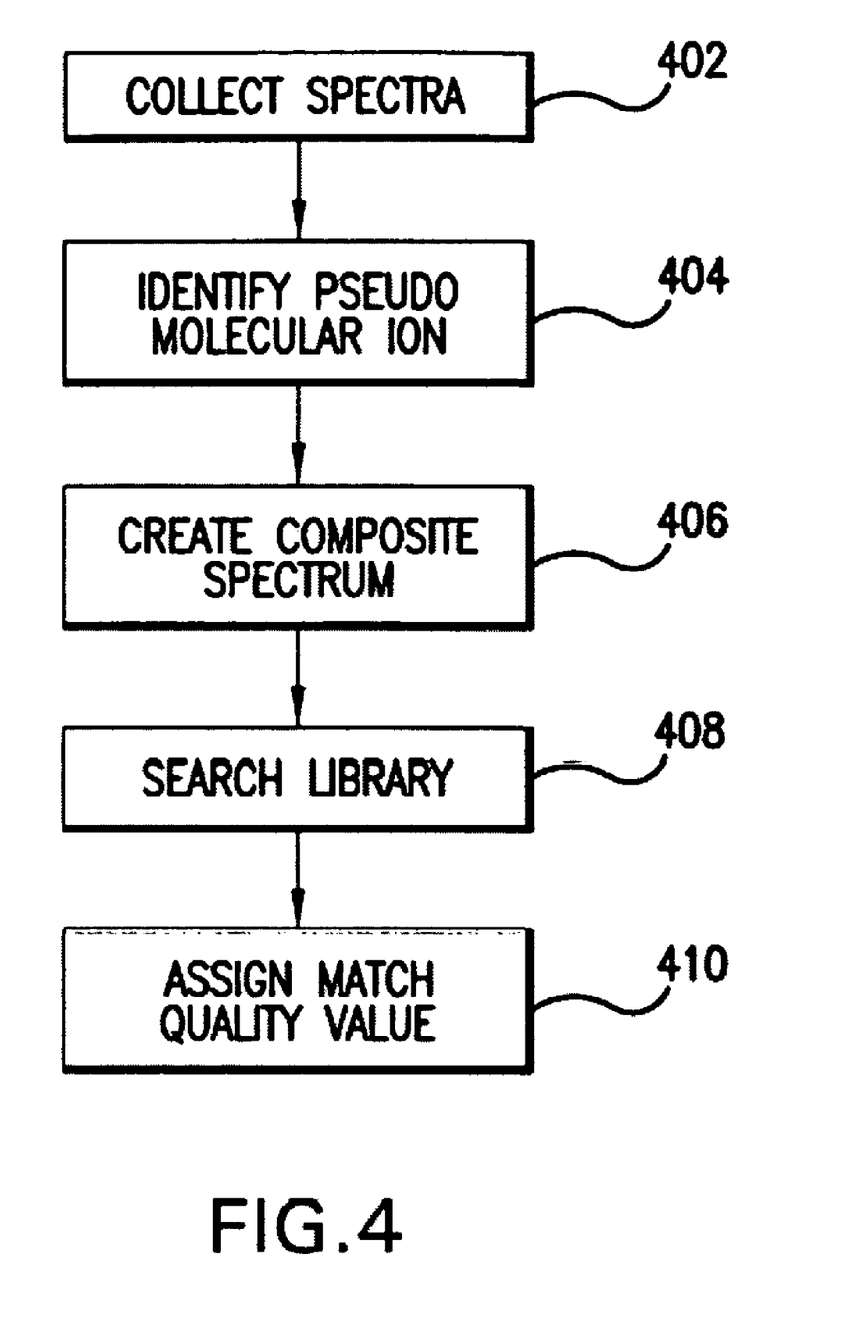
FIG. 4 depicts a flow chart illustrating a method identifying unknown molecular compounds.
Figure 5:
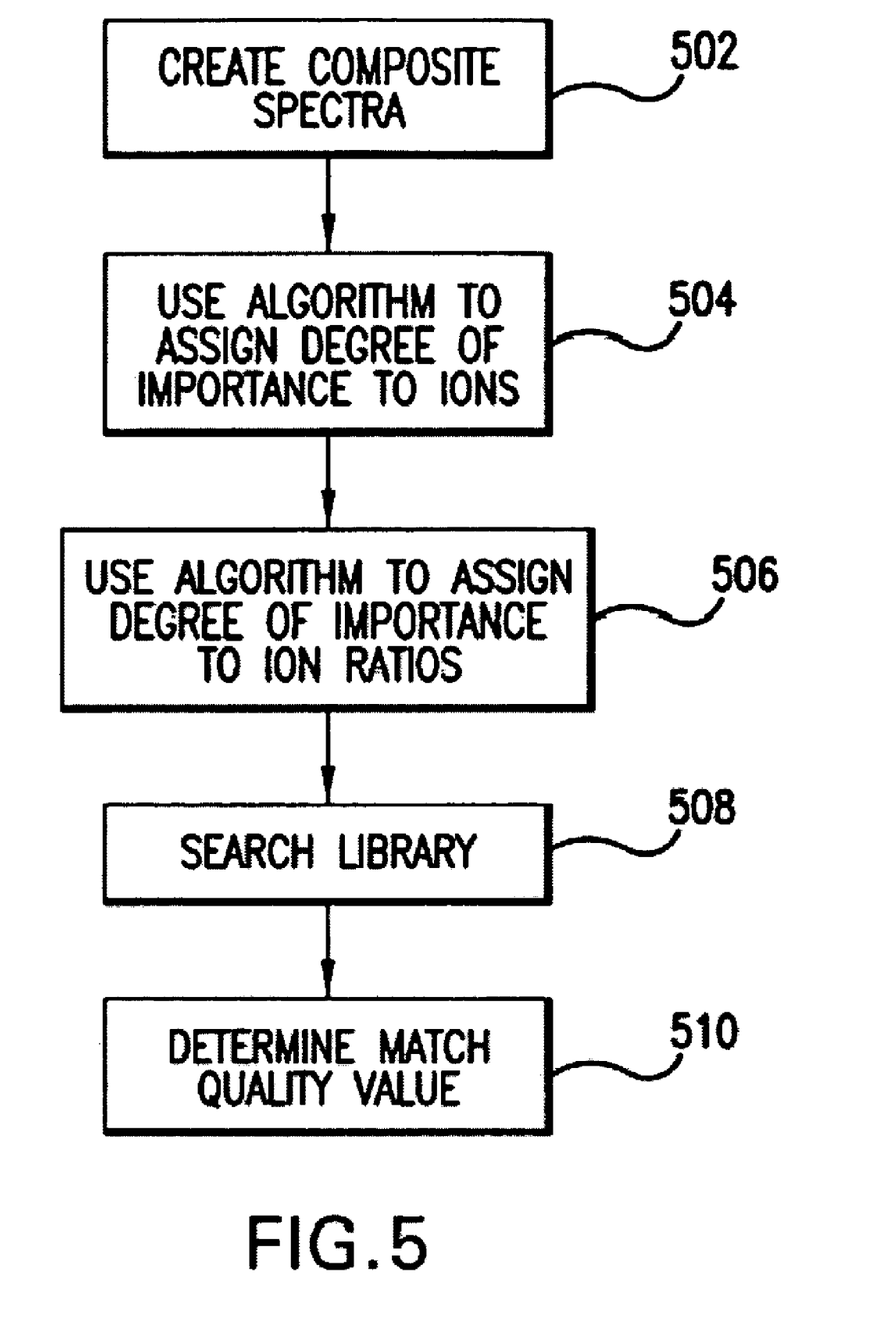
FIG. 5 depicts a flow chart illustrating another method of identifying unknown molecular compounds.

The flow charts of FIGS. 4 and 5 show embodiments of the architecture, functionality, and operation of possible implementations of software that may be used to operate the systems and methods described above. In this regard, each block may represent a module, segment, or portion of code, which includes one or more executable instructions for implementing the specified logical functions. It should also be noted that in some implementations, the functions noted in the blocks may occur out of the order indicated by the figures. For example, two blocks shown in succession may in fact be executed substantially concurrently or the blocks may sometimes be executed in the reverse order, depending upon the functionality involved, as would be understood by those reasonably skilled in the art.

FIG. 4 of the drawings provides a flow chart illustrating a method for identifying unknown molecular compounds using adducts, dimers and/or oligomers. First, various spectra are collected at various collision energies (step 402). Next the pseudo molecular ion is identified (step 404). Having tentatively identified this ion (usually in the spectrum with the lowest collision energy for which one or more ions are produced), any ions with higher molecular weight can be ignored, which may be represented in reduced spectra. The pseudo molecular ion may be a molecular ion cluster that includes the most abundant molecular ion and all related ions resulting from the inclusion of naturally occurring isotopes of the elements that make up the molecule. A reduced spectrum is a spectrum with masses above the pseudo molecular ion clipped off or ignored. Spectra collected at higher energies are likely to have more fragment ions and may or may not display the pseudo molecular ion. Since the pseudo molecular ion has been determined, ions with higher molecular weight can be ignored in these spectra too.

A composite spectrum is then created out of the reduced spectra (step 406). The composite spectrum is then searched against a library of known composite spectra (step 408). A match quality value is then assigned that is a measure of the fit between the unknown and library spectra (step 410). The presence of appropriate adduct, dimer, or oligomer ions in the original spectra can be factored into this match quality value, even though the adduct, dimer, or oligomer ions were not included when comparing the unknown spectrum to the library spectra.

FIG. 5 is a flow chart illustrating another method of using adduct, dimer, or oligomer ions to help identify an unknown pseudo molecular ion. First, a composite spectrum is created from multiple spectra collected at varying collision energies (step 502). The composite spectrum may include all observed adduct, dimer and oligomer ions. Next, an algorithm is used to assign a degree of importance (weight factor) to the ions depending upon the identity of the ions (pseudo molecular ion, fragment ion, adduct ion, dimer, etc.) (step 504). An algorithm may also be used to assign a degree of importance to the ion ratios depending upon ion identity (step 506). For example, the ratios of adduct, dimer, and/or oligomer ions to each other or to the pseudo molecular ion could be given a small weighting factor (little importance); or, ion ratios for the pseudo molecular ion and its fragment ions could be given a large weighting factor (high importance). The composite spectrum is then searched against a library of composite spectra that includes adduct, dimer, and oligomer ions (step 508). A match quality value is then determined that takes into account any or all ions in the spectrum along with the ratios and importance of the ions (step 510).

In cases where peaks overlap and the background cannot be subtracted easily, deconvolution algorithms (such as the Automated Mass Spectral Deconvolution and Identificiation System ["AMDIS"] software offered by the National Institute of Standards and Technology ["NIST"]) could be used to pull the individual spectra apart prior to the application of techniques described hereinabove.

Figure 6:
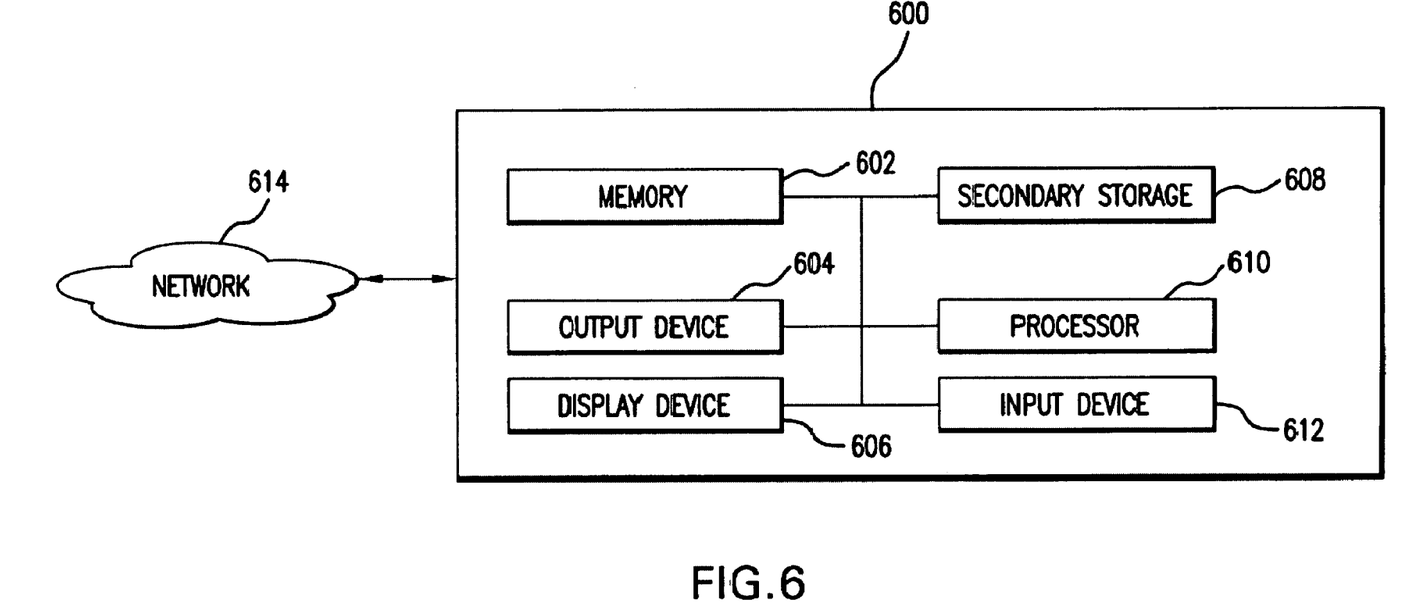
FIG. 6 depicts a computer that may be used to perform one method for mass spectrometry dynamic library searching.

FIG. 6 illustrates exemplary hardware components of a computer 600 that may be used to perform the Dynamic Library Searching. The computer 600 includes a connection with a network 614, such as the Internet or other type of computer or telephone networks. The computer 600 typically includes a memory 602, a secondary storage device 608, a processor 610, an input device 612, a display device 606, and an output device 604.

The computer system 600 may be a general purpose computer system which is programmable using a high level computer programming language, such as "C," "C++" "Pascal," "Visual Basic" or other language. The computer system may also be specially programmed, special purpose hardware. In a general purpose computer system, the processor 610 is typically a commercially available processor, of which the series x86 processors, including a Pentium processor using MMX extensions available from Intel, and the 680X0 series microprocessors available from Motorola are examples. Many other processors are available. Such a microprocessor executes a program called an operating system, of which Windows95, WindowsNT, Windows2000, WindowsXP, UNIX, DOS and VMS are examples, which controls the execution of other computer programs and provides scheduling, debugging, input/output control, accounting, compilation, storage assignment in a file system containing named files of data, data management and memory management, communication control, protection and related services. The processor 602 and operating system define a computer platform for which application programs in high-level programming languages are written. It should be understood the other embodiments may employ other computer platforms, processors, or high-level programming languages. Additionally, the computer 600 may be a multiprocessor computer system, may include multiple computers connected over a computer network, or may be incorporated in the MS system.

The memory 602 may include random access memory (RAM) or similar types of memory. The secondary storage device 608 may include a hard disk drive, floppy disk drive, CD-ROM drive, magnetic disk, flash memory, tape or other types of non-volatile data storage, and may correspond with various databases or other resources. The disk may be removable, known as a floppy disk, or permanent, known as a hard drive. A disk has a number of tracks in which signals are stored, typically in binary form, i.e., a form interpreted as a sequence of one and zeros. Such signals may define, for example, an application program to be executed by the microprocessor, or information stored on the disk to be processed by the application program.

The processor 610 executes information stored in the memory 602, the secondary storage 608, or received from the Internet or other network 614. Typically, in operation, the processor 610 causes data to be read into an integrated circuit memory element, which is typically a volatile, random access memory such as a dynamic random access memory (DRAM) or static memory (SRAM). The integrated circuit memory element allows for faster access to the information by the processor than does the disk. The processor generally manipulates the data within the integrated circuit memory and copies the data to and from the disk if the data are not being used. A variety of mechanisms are known for managing data movement between the disk and the integrated circuit memory element, and any such mechanisms may be employed. Similarly, any memory system may be employed.

The input device 612 may include any device for entering data into the computer 600, such as the mass spectrometer, a keyboard, keypad, cursor-control device, or touch-screen (possibly with a stylus). The display device 606 may include any type of device for presenting visual image, such as, for example, a computer monitor, flat-screen display, or display panel. The output device 604 may include any type of device for presenting data in hard copy format, such as a printer, and other types of output devices including speakers or any device for providing data in audio form. Output could be to a file on the same or another computer. The computer 600 can possibly include multiple input devices, output devices, and display devices.

Although the computer 600 is depicted with various components, one skilled in the art will appreciate that the computer 600 can contain additional or different components. In addition, although aspects of an implementation consistent with the present disclosure are described as being stored in memory, one skilled in the art will appreciate that these aspects can also be stored on or read from other types of computer program products or computer-readable media, such as secondary storage devices, including hard disks, floppy disks, or CD-ROM; a carrier wave from the Internet or other network; or other forms of RAM or ROM. The computer-readable media may include instructions for controlling the computer 600 to perform a particular method.

The foregoing description of the present invention provides illustration and description, but is not intended to be exhaustive or to limit the invention to only the embodiments disclosed. For example, the above method of generating and searching a reference library of known compounds is described in connection with LC-MS; however, it is to be understood that the above described methods can be used with any type of analysis that produces multiple variable results for unknown compounds. Modifications and variations are possible consistent with the above teachings or may be acquired from practice of the invention. Thus, it is noted that the scope of the invention is defined by the claims and their equivalents.

What is claimed is:

1. A method for accounting for adducts in spectra to make library searching more reliable, said method including the steps of:
    (i) collecting multiple spectra at varying collision energies from a mass spectrometer;
    (ii) identifying a pseudo molecular ion;
    (iii) using said multiple spectra to create reduced spectra;
    (iv) creating a composite spectrum out of said reduced spectra;
    (v) searching against a library of known composite spectra for said composite spectrum; and
    (vi) assigning a match quality value, said match quality value indicative of a measure of the fit between the composite spectrum and the library of known composite spectra.

2. The method according to claim 1, wherein the pseudo molecular ion is identified in the multiple spectra with the lowest collision energy for which one or more ions are produced.

3. The method according to claim 1, wherein said reduced spectra ignore ions with masses above the pseudo molecular ion.

4. The method according to claim 1, wherein said pseudo molecular ion is a pseudo molecular ion cluster, said molecular ion cluster comprising a most abundant molecular ion and all related ions resulting from the inclusion of naturally occurring isotopes of elements that make up said most abundant molecular ion.

5. The method according to claim 1, wherein the steps are performed by an executable program.

6. The method according to claim 1, wherein the step of assigning a match quality value further includes the factoring in the presence of adduct, dimer, or oligomer ions in the original spectra into the match quality value, wherein said presence of adduct, dimer, or oligomer ions is assigned a weighting factor of small significance.

7. The method according to claim 1, wherein said mass spectrometer is a liquid chromatograph-mass spectrometer.

8. The method according to claim 1, wherein said multiple spectra are generated from atmospheric pressure ionization and collision induced dissociation.

9. A method for identifying a pseudo molecular ion in a spectrum, said method including the steps of:
    (i) creating a composite spectrum from multiple spectra, said multiple spectra collected at varying collision energies from a mass spectrometer; and
    (ii) using a first dynamic algorithm for assigning a degree of importance to ions depending upon the identity of said ions.

10. The method according to claim 9, further including the step of (iii) using a second dynamic algorithm for assigning a degree of importance to the ion ratios depending upon the identity of said ions.

11. The method according to claim 10, further including the step of:
    (iv) searching said composite spectrum against a library of composite spectra, said library of composite spectra including adduct, dimer, and oligomer ions.

12. The method according to claim 11, further including the step of:
    (vi) determining a match quality value, said match quality value taking into account any or all ions in the spectrum along with the ions' ratios and degrees of importance.

13. The method according to claim 10 wherein the ratios of adduct, dimmer, and/or oligomer ions to each other or to the pseudo molecular ion are given a weighting factor of small significance.

14. The method according to claim 10 wherein the ion ratios for the pseudo molecular ion and fragment ions are given a weighting factor of large significance.

15. The method according to claim 9, wherein said mass spectrometer is a liquid chromatograph-mass spectrometer.

16. The method according to claim 9, wherein said multiple spectra are generated from atmospheric pressure ionization and collision induced dissociation.

17. The method according to claim 9, wherein the steps are performed by an executable program.

18. The method according to claim 12, wherein said first dynamic algorithm and said second dynamic algorithm are modified and said step of determining a match quality value is repeated.

19. A system for searching a reference library of known compounds, said system including:
    (i) a mass spectrometer, said mass spectrometer generating multiple spectra collected at varying collision energies for an unknown compound;
    (ii) a reference library; and
    (iii) a computer;
        (a) for creating a composite spectrum from said multiple spectra, said composite spectrum indicating a pseudo molecular ion and fragment ions,
        (b) for assigning a degree of importance to the ion ratios depending upon the identity of said ions, and
        (c) for searching said reference library using said composite spectrum.

20. The system according to claim 19, wherein said computer determines a match quality value, said match quality value taking into account any or all ions in the composite spectrum along with the ions' ratios.

21. The system according to claim 19, wherein said reference library stores multiple spectra for each known compound.

22. The system according to claim 19, wherein said mass spectrometer is a liquid chromatograph-mass spectrometer.

23. The system according to claim 19, wherein said composite spectra are generated from atmospheric pressure ionization and collision induced dissociation.

24. The system according to claim 20, wherein the ratios of adduct, dimmer, and/or oligomer ions to each other or to the pseudo molecular ion are given a weighting factor of small significance in the determination of said match quality value.

25. The system according to claim 20, wherein the ion ratios for the pseudo molecular ion and fragment ions are given a weighting factor of large significance in the determination of said match quality value.

26. A computer readable medium, said computer readable medium including instructions to cause a computer to:
   (i) create a composite spectrum from multiple spectra, said multiple spectra collected at varying collision energies; and
   (ii) use first a dynamic algorithm for assigning a degree of importance to ions depending upon the identity of said ions.

27. The computer readable medium according to claim 26, further including instructions to cause said computer to:
   (iii) use a second dynamic algorithm for assigning a degree of importance to the ion ratios depending upon the identity of said ions.

28. The computer readable medium according to claim 27, further including instructions to cause said computer to:
   (iv) search said composite spectrum against a library of composite spectra, said library of composite spectra including adduct, dimer, and oligomer ions.

29. The computer readable medium according to claim 28, further including instructions to cause said computer to:
   (v) determine a match quality value, said match quality value taking into account any or all ions in the spectrum along with the ions' ratios.

30. The computer readable medium according to claim 29, wherein the ratios of adduct, dimmer, and/or oligomer ions to each other or to the pseudo molecular ion are given a weighting factor of small significance in the determination of said match quality value.

31. The computer readable medium according to claim 29, wherein the ion ratios for the pseudo molecular ion and fragment ions are given a weighting factor of large significance in the determination of said match quality value.

* * * * *

UNITED STATES PATENT AND TRADEMARK OFFICE
CERTIFICATE OF CORRECTION

PATENT NO. : 6,936,813 B2
DATED : August 30, 2005
INVENTOR(S) : Zavitsanos et al.

It is certified that error appears in the above-identified patent and that said Letters Patent is hereby corrected as shown below:

Column 10,
Line 53, after "computer" delete ";" and insert -- , --, therefor.

Signed and Sealed this

Thirteenth Day of December, 2005

JON W. DUDAS
*Director of the United States Patent and Trademark Office*